United States Patent [19]

Ferreira Vigouroux et al.

[11] Patent Number: 4,915,941
[45] Date of Patent: Apr. 10, 1990

[54] METHOD FOR PREVENTING THE DEVELOPMENT OR DECREASING THE EXTENT OF MALARIAL PARASITEMIA

[75] Inventors: Arturo Ferreira Vigouroux, Santiago, Chile; Victor Nussenzweig, New York, N.Y.

[73] Assignee: New York University, New York, N.Y.

[21] Appl. No.: 940,510

[22] Filed: Dec. 11, 1986

[51] Int. Cl.$^4$ .............................................. A61K 45/02
[52] U.S. Cl. ................................... 424/85.5; 424/85.4
[58] Field of Search .................................. 424/85, 85.5

[56] References Cited

PUBLICATIONS

Chemical Abstracts, vol. 73, Abstract No. 119008j, 1970.
Chemical Abstracts, vol. 104, Abstract No. 223312v, 1986.
Chemical Abstracts, vol. 105, Abstract No. 170299h, 1986.
Chemical Abstracts, vol. 77, Abstract No. 28659k, 1972.

Primary Examiner—Blondel Hazel
Attorney, Agent, or Firm—Darby & Darby

[57] ABSTRACT

A method for inhibiting the development or limiting the extent of malarial parasitemia in mammals comprising administering an amount of gamma-interferon sufficient to inhibit parasitemia, said parasitemia being incident to invasion of said mammal by sporozoites of a member of the genus Plasmodium. The administration of gamma-interferon takes place no later than the end of the prepatency period of said mammal (or of the dormant phase of the parasite as the case may be).

19 Claims, 4 Drawing Sheets

METHOD FOR PREVENTING THE DEVELOPMENT OR DECREASING THE EXTENT OF MALARIAL PARASITEMIA

FIELD OF THE INVENTION

This invention relates to the use of gamma-interferon to combat malaria infection. More particularly, this invention relates to the use of gamma-interferon to inhibit the development and to limit the extent of parasitemia in mammals infected with malarial sporozoites.

BACKGROUND OF THE INVENTION

Malaria is a protozoan disease transmitted to mammals, including humans, by the bite of Anopheles mosquitoes. The causative organisms are protozoa of the genus Plasmodium. The sporozoite stage of the parasite lives in the salivary glands of Anopheles mosquitoes from where it is transmitted to mammals.

Four species of Plasmodium are infective to humans. They are *P. falciparum, P. vivax, P. ovale* and *P. malariae*. Other species of the parasite are infective in other mammalian species.

Despite years of extensive efforts to eradicate the disease, malaria remains a major worldwide public menace, affecting more than 150,000,000 people in any given year. Combatting malarial infections has become more difficult in recent years due to the spread of drug-resistant parasites (and insecticide-resistant mosquitoes), in many areas. The occurrence of several epidemic outbreaks of this disease lends particular urgency to any efforts designed to combat malaria.

Although the life cycle of Plasmodium is complex, it is well understood in general outline. Nevertheless, much remains to be understood at the biochemical and genetic levels. The organism undergoes distinct morphological changes, involving the participation of a mammalian host and a mosquito vector. Human infection begins when a female mosquito introduces plasmodial sporozoites into the blood system while feeding. After a brief period of time in the peripheral blood, these organisms migrate to the liver. There, they invade hepatocytes where they undergo a morphological change to merozoites and initiate the preclinical exo-erythrocytic phase of the disease. By a process of asexual multiplication, a single sporozoite can eventually produce approximately $10^4$ hepatic haploid forms termed merozoites. From the liver, the parasite is released to the bloodstream and invades the red blood cells, where it continues its development and asexual multiplication.

International efforts to control or prevent malarial infections in individuals have been only partly successful. Control measures have been directed toward reducing the population levels of the Anopheles mosquito vector, improvement in public health and sanitary procedures, and administration of drugs for both prophylaxis and treatment of individuals at risk.

An alternative approach is based upon the use of monoclonal antibodies capable of inactivating sporozoites, the primary infective agent (Nussenzweig, et al., U.S. Pat. No. 4,466,917; Nussenzweig, et al., pending U.S. patent application Ser. No. 574,124). In addition to the foregoing, vaccines are being developed comprising antigenic peptides and proteins derived from the various Plasmodium species (Nussenzweig, et al., U.S. Pat. No. 4,466,917; Nussenzweig, et al., pending U.S. patent application Ser. No. 574,124; Nussenzweig, et al., pending U.S. patent application Ser. No. 574,553; Ellis et al., pending U.S. patent application Ser. No. 633,147; Nussenzweig, et al., pending U.S. patent application Ser. No. 649,903; Schlesinger, et al., pending U.S. patent application Ser. No. 695,257; Nussenzweig, et al., pending U.S. Pat. No. 716,960; and Arnot, et al., pending U.S. patent application Ser. No. 764,645, all incorporated by reference). The use of these materials, directed against the sporozoite stage of the malaria parasite, is capable of providing protection against sporozoite infection in both animals and humans. However, the specific nature of these materials makes it necessary to use immunogens or monoclonal antibodies directed against all of the known Plasmodia which infect humans in order to insure protection from the disease.

The use of appropriate drugs can suppress symptoms in infected individuals living in endemic areas or cure malarial infection completely. Chloroquine and its derivatives have been used successfully in the treatment of malaria. Pyrimethamine, an antifolate agent, has also been effective in the treatment of malaria. Where the drug-resistant forms exist, chloroquine plus pyrimethamine have been used. However, both of these drugs have potential side effects. Chloroquine can induce hemolytic anemia while pyrimethamine can cause megaloblastic anemia. Moreover, as mentioned above, the occurrence of new drug-resistant strains of the malaria parasite has made combatting malarial infestations more difficult.

Interferons are a family of inducible, antiviral proteins and glycoproteins produced by most eukaryotic species in response to a wide variety of viral and non-viral inducers. Three distinct major species of interferons have been characterized and can be distinguished by their physiochemical properties and amino acid sequences, which are quite different. Alpha-interferons are the major species produced by incubating viruses with cells of lymphoid origin. Beta-interferons are the major species produced by nonlymphoid cells upon induction with viral or non-viral agents. Gamma-interferons are the major species produced by lymphocytes (T cells in particular) upon treatment with mitogens, or by sensitized lymphocytes upon treatment with specific antigens. Interferons of all three species are antiviral proteins but also possess other non-antiviral activities of different types and/or in different degrees.

Inducers of alpha- and beta-interferons have been studies for their anti-malarial effect (Jahiel, et al., Nature 220: 710-711, 1968; Jahiel, et al., Science 161: 802-804, 1968). In these articles, statolon, Newcastle disease virus (NDV), and a double-stranded copolymer of polyriboinosinic acid and polyribocytidylic acid (all three now known to induce only alpha- and beta-interferons) were administered to mice before or after infecting the mice with *P. berghei* sporozoites or with the blood form of this parasite.

The interferon inducers are said to have prolonged the prepatency period to a statistically significant extent, especially which administered within 16-24 hours after sporozoite administration. This effect was much less pronounced against the blood forms of the parasite, or when inducers were administered prior to or later than 24 hours after sporozoite injection. The authors hypothesized—but did not demonstrate—that the protective effect was due to interferon.

It should be noted that interferons manifest a diverse range of antiviral, anticellular and immunoregulatory activities which are dependent upon the specie of interferon employed and the cell type acted upon. It is difficult today (and impossible during the era of the above-cited Jahiel references) to analyze in vivo results and ascribe them to a specific "immunoregulatory", or other, effect of interferon treatment.

OBJECTS OF THE INVENTION

The present invention has several objects including, but not limited to, the following:

to provide a method for combatting mammalian malaria;

to provide a method for combatting mammalian malaria as an adjunct to immunization and/or drug therapy;

to provide a method for preventing patency in mammals infected with malarial sporozoites;

to provide a method for prolonging the prepatency period in mammals infected with malarial sporozoites;

to provide a method for limiting the extent of parasitemia in mammals infected with malarial sporozoites;

to provide a method for preventing patency in immunized mammals invaded with malarial sporozoites;

to provide a method for enhancing the efficacy of anti-malarial drugs;

to provide a method for decreasing the severity of malarial infection;

to provide a method for inhibiting the development of exoerythrocytic forms of the parasite.

These and other objects of the present invention will be apparent to one or ordinary skill in the art in light of the present description, accompanying claims and appended drawings.

SUMMARY OF THE INVENTION

The present inventors have now found that, even in small quantities, gamma-interferon is effective in preventing patency, prolonging the prepatency period, and limiting the extent of parasitemia in mammals infected with malarial sporozoites. In particular, the present inventors have found that gamma-interferon is surprisingly effective in limiting parasitemia, when used alone or in combination with other anti-malarial agents. Further, the inventors have found that even a single gamma-interferon treatment administered before patency has a considerable limiting effect on the initial parasitemia and can be advantageously employed in conjunction with other anti-malarial agents.

The beneficial results described above are obtained by administering to a mammal an effective amount of interferon prior to, or after, invasion of said mammal with malarial sporozoites (but before patency of said mammal). Preferably, gamma-interferon administration is repeated and most preferably it is initiated prior to infection and repeated at least once post-infection.

Parasitemia is defined as presence of at least one parasite in 10,000 blood cells. Patency is defined by the first visual (microscopic) observation of at least one parasite in 10,000 blood cells.

DETAILED DESCRIPTION OF THE INVENTION

The invention is described in detail below by reference to specific and preferred embodiments. The purpose of this is to illustrate the present invention without limiting its scope.

EXAMPLE 1

Effect of Gamma-Interferon Administered Post-Infection

Five groups of three-month old female A/J mice (Jackson Laboratories, Bar Harbor, ME) were injected with tenfold dilutions of recombinant murine gamma-interferon (or phosphate-buffered saline for the controls) five hours before the intravenous injection of 5,000 sporozoites obtained from the salivary glands of *Anopheles stephensi* mosquitos. The interferon was obtained from Genentech, Inc., San Francisco, CA 94080, but the source should not be important. Of course, natural purified murine gamma-interferon could have been used instead.

Figure 1:
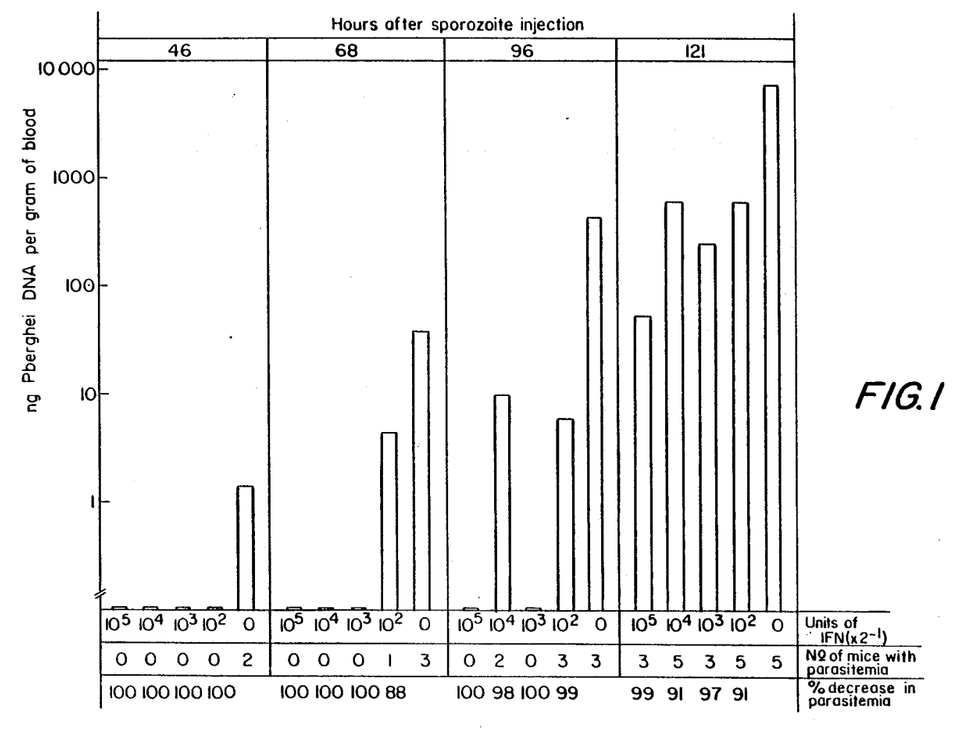
FIG. 1 is a bar graph demonstrating the effectiveness of gamma-interferon treatment in the inhibition of EEF development in mice.

The mice were bled from the ventral vein and artery of the tail at the intervals indicated at the top of FIG. 1. Blood samples were spun down, the red cells were washed once with phosphate-buffered saline (PBS), pH 7.2, resuspended in 1M PBS containing 0.015% (w/v) Saponin (Sigma, St. Louis, MO), incubated at 37° C. for five minutes and spun down. To the pellet, which contained parasites and white cell nuclei, 50 micrograms of normal rat liver DNA were added as a carrier and total DNA was extracted as described under "DNA Extraction" below.

The DNA content of each blood sample was immobilized in 1.5 cm diameter, 0.45 millimicron pore-size nitrocellulose filters (Millipore Corp., Bedford, MA) and hybridized with a genomic 2.2 kb repetitive *P. berghei* DNA probe (obtained as described under "Preparation of DNA Probe", below), labelled with $^{32}P$ by nick translation. To calculate background levels, filters containing (a) DNA from normal mouse blood and (b) carrier rat DNA were included in the hybridization assays. A standard hybridization curve was constructed by probing 10-fold dilutions of blood-stage *P. berghei* DNA. A linear relationship between the radioactivity associated with the filters and the amount of parasite DNA immobilized was always obtained in the range of 100 picograms to one microgram *P. berghei* DNA (Preparation of DNA Probe and FIG. 4). The amounts of the parasite DNA associated with the filters were calculated by reference to the standard curve and expressed as the means and standard deviations of the nanograms of *P. berghei* DNA detected in five animals. These values are represented in FIG. 1 in a logarithmic scale. Blood smears were prepared to measure parasitemia (a total of $10^4$ per slide were counted). The percent decrease in parasitemia was calculated from the hybridization experiment, by comparing the values obtained for the mammals pretreated with recombinant murine gamma-interferon with those obtained in placebo-treated mammals. The results are shown in FIG. 1.

As can be seen in FIG. 1, mice injected once with the largest amount of gamma-interferon did not develop detectable parasite DNA until approximately the fifth day after infection. Control mice injected with placebo had demonstrable parasite DNA in their blood smears 46 hours post-infection, and by the fifth day post-infection 100% of the mice had developed parasitemia. As can be seen in FIG. 1, interferon treatment at all dilutions prolonged the prepatency period, but after a single interferon treatment, by 121 hours Post-infection all mice had detectable parasite DNA in their blood. However, interferon treatment led to a 91–99% decrease in parasitemia in infected anmials. Thus, a single gamma-interferon treatment after sporozoite infection led to an increase in the prepatency period and a considerable decrease in the numbers of the para site that reach the bloodstream.

Since the extent of parasitemia is a measure of the severity of the disease treatment with gamma-interferon helps to decrease the severity of the disease.

It should be noted that the sporozoite dose received by each mouse (5,000 sporozoites) was one order of magnitude higher than that normally received by mice (or humans) by infection through a mosquito vector. This means that in an actual infection much fewer sporozoites would have been present.

By contrast, the interferon doses given were not very high.

All of this shows that the results obtained in this and the following experiments were surprising in terms of the observed decrease in parasitemia in the gamma-IFN-treated mice.

EXAMPLE 2

Mode of Gamma-Interferon Action

The inventors next examined the development of exoerythrocytic forms (EEF) of *P. berghei* in rats untreated or treated with gamma-interferon in an effort to specify the mode of interferon action. Groups of two to four-month old female Norway Brown rats (Charles River, Wilmington, MA) were injected i.v. with different amounts of recombinant rat gamma-interferon (obtained from Drs. H. Schellekems and P.v.d. Meide, Primate Center TNO, Rijswijk, Netherlands; but again, the source of rat gamma interferon does not affect the present results) five hours before the i.v. injection of $10^5$ *P. berghei* sporozoites, obtained from the salivary glands of *Anopheles stephensi* mosquitos. Seven different experiments were carried out, each including a positive control obtained by pretreating the rats with a 400 microliter injection of the solvent used to prepare the interferon dilutions (1% heat-inactivated normal rat serum in PBS).

Forty-four hours after sporozoite infection, the rats were bled from the axillary vein and artery and their livers were removed. DNA from these organs was purified and probed for the presence of *P. berghei* DNA. Values, expressed as means and standard deviations, represent the percent inhibition of EEF development and were obtained by comparing the amount of hepatic parasite DNA present in interferon- and placebo-treated groups.

Figure 2:
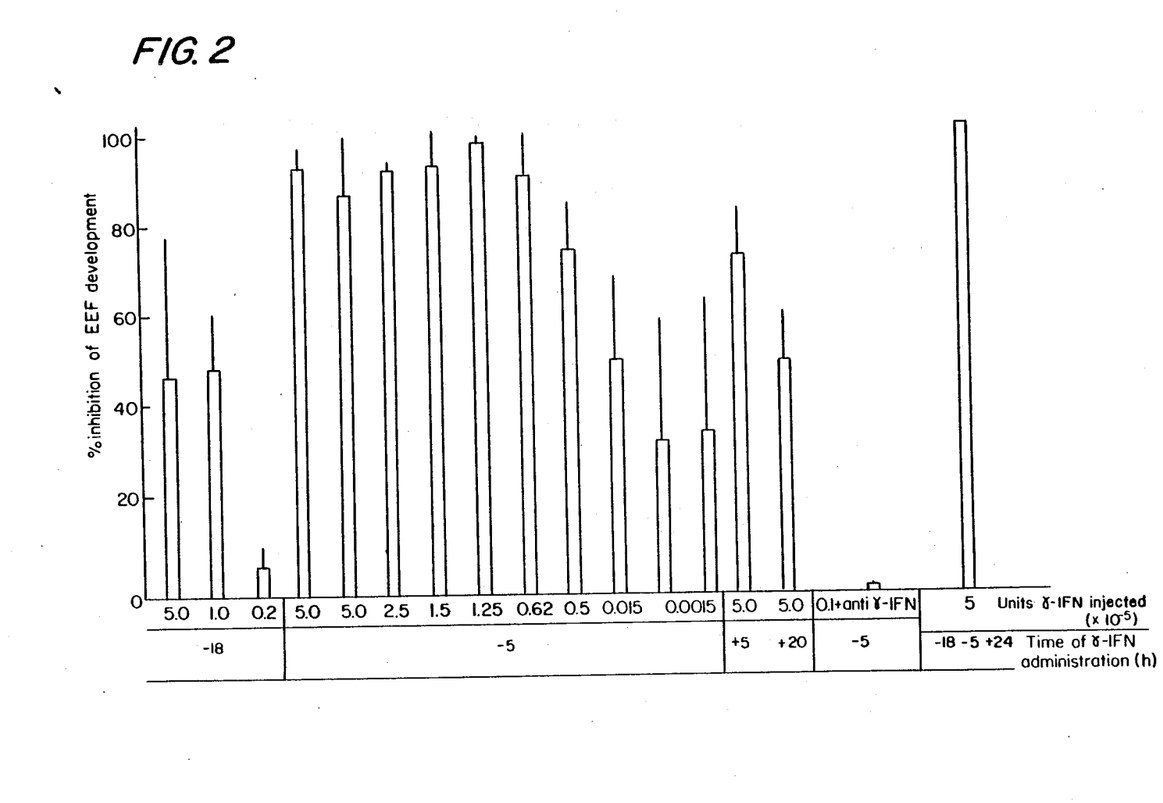
FIG. 2 is a bar graph demonstrating the effects of different gamma-interferon doses on the inhibition of EEF development in Norway Brown rats.

The results are presented in FIG. 2. The time of interferon injection is expressed in hours relative to the time of sporozoite injection (time 0). Thus, in the group shown at the extreme right of this figure, three injections of $5 \times 10^5$ units of interferon were performed 18 and 5 hours before sporozoite injection and 24 hours afterwards. In one experiment (second bar from right), interferon activity was strongly inhibited by preincubating it for 45 minutes on ice with two neutralizing doses of a polyclonal rabbit anti-[rat gamma-interferon] antibody (Drs. H. Schellekens and P.v.d. Meide, Primate Center TNO, Rijswijk, Netherlands). As a control, interferon was incubated with an equivalent amount of normal rabbit serum.

As can be seen in FIG. 2, treatment of rats with either $5 \times 10^5$ or $1 \times 10^5$ units of interferon 18 hours before the injection of sporozoites led to a 50% inhibition in EEF development. Doses of $1.5 \times 10^3$ to $5 \times 10^5$ units of interferon given at five hours before infection led to at least a 50% inhibition of EEF development and at the higher doses, interferon treatment led to a greater than 90% inhibition of EEF. Interferon was effective in inhibiting EEF even when given once as late as 20 hours post-injection of sporozoites. As mentioned above, anti-gamma-interferon antibodies were capable of totally neutralizing the effect of gamma-interferon, and full EEF development ensued. When rats were given $5 \times 10^5$ units of gamma-interferon at $-18$, $-5$ and $+24$ hours relative to infection, EEF development was inhibited 100%. These results confirm that, and help explain how, interferon inhibits parasitemia and lengthens the prepatency period. They also demonstrate that interferon has at least an attenuating role in the severity of the disease by reducing the number of exoerythrocytic forms of the parasites developed in the liver.

EXAMPLE 3

Inhibition of *P. vivax* Infectivity in Chimpanzees Pretreated with Interferon

In order to test the efficacy of gamma-interferon treatment in the species closer to humans then either the rat or mouse models, chimpanzees were treated with recombinant human gamma-interferon (M. Shepard, Genentech, Inc., San Francisco, CA) prior to and after challenge with *P. vivax* sporozoites. Four adult male chimpanzees (*Pan troglodytes*), weighing 55–65 kg (maintained at the New York University laboratory for Experimental Medicine and Surgery in Primates) were used in this experiment. Two of them were injected i.v. with $5 \times 10^6$ units recombinant human gamma-interferon at $-5$ hours, $+2$ hours and on days 1–7 post-infection; the other two received placebo phosphate-buffered saline (PBS) injections. At time 0, all four mammals were challenged with an i.v. injection of $10^5$ *P. vivax* sporozoites, freshly obtained from the salivary glands of *Anopheles stephensi* mosquitos. On day 7, the animals were splenectomized. This was done to facilitate the detection of blood stage parasites since the spleen is known to inhibit parasitemia. Two blood smears per animal were prepared starting on day 10 and every other day thereafter, until all mammals became patent. A total of $10^4$ red blood cells were counted per slide. Results are expressed as percent parasitemia per mammal and are shown in FIG. 3.

Figure 3:
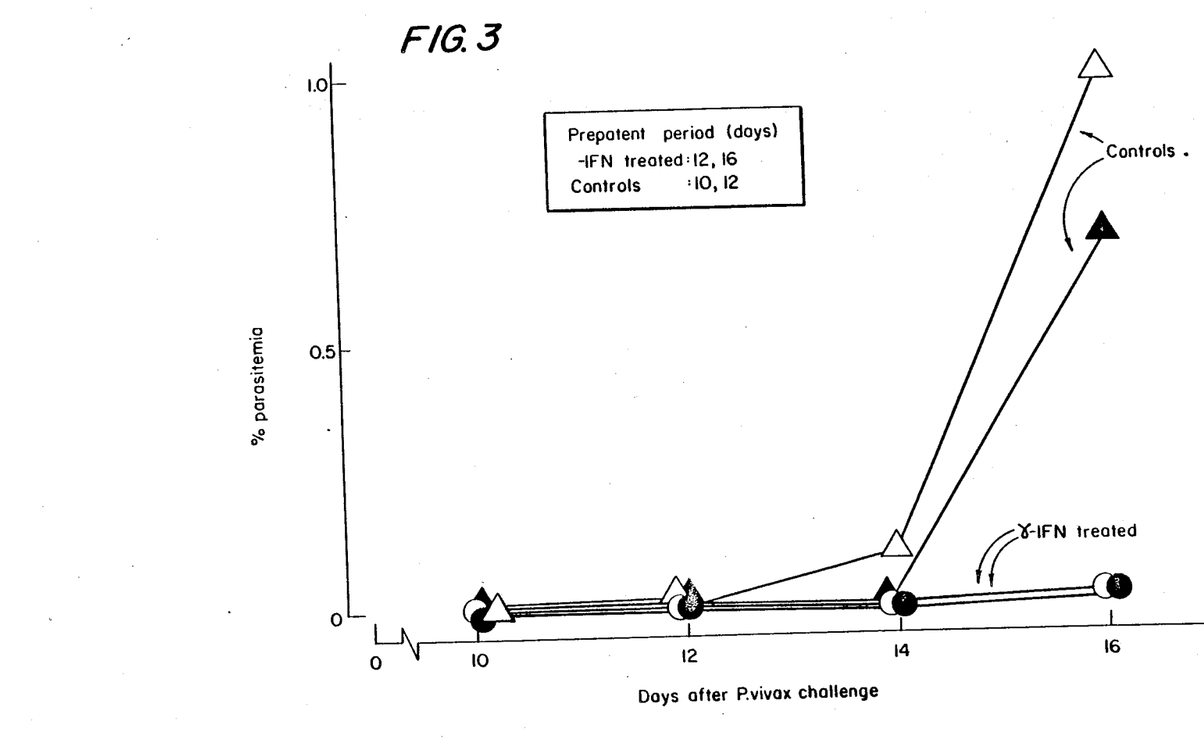
FIG. 3 is a graph demonstrating the inhibition of EEF development on chimpanzees by gamma-interferon.

FIG. 3 shows that gamma-interferon treatment again led to a considerable delay in the appearance of parasites in the blood stream and increased the prepatent period over control mammals. Gamma-interferon also limited the extent of parasitemia. This is an important result because it uses a model closer to humans (chimpanzees) than either the rat or the mouse model, and employs a specie of Plasmodium which is infectious for humans.

The primates used for these experiments were also injected with much larger amounts of sporozoites than would be normally received if infection had resulted from mosquito bites. Moreover, the chimpanzees were immunocompromised by spleen removal.

All of these conditions indicate that the efficacy of gamma-IFN in combatting parasitemia would be greater under normal infection conditions. Thus, the fact that the experimental primates and other animals tested eventually developed parasitemia does not detract from the utility of the present invention.

The experiments described above show at a minimum that the prepatency period of mammals can be significantly prolonged with administration of gamma-interferon prior to and preferably after infection with sporozoites. Most preferably, interferon doses are administered more than once, but must be administered while development of the parasite is taking place in the liver. Once parasitemia is established, interferon has no substantial effect.

The most preferred dosage regimen is one that includes at least one interferon injection prior to infection and preferably repeated injections after infection.

The amount of interferon used in the foregoing experiments was relatively small and was administered in one or two doses. Patency will be ultimately avoided by continued use of gamma-interferon at large (non-toxic) doses. This will be true of humans, also, although the present inventors did not conduct actual experiments with humans because the use of gamma-interferon in humans is still limited.

It is expected, that the minimum effective amount for humans will be of the same order as that given to the monkeys in the present examples. It is difficult to predict a maximum amount because the toxicity of gamma-interferon to humans has not been established. Of course, if gamma-interferon is used alone, more than three treatments will be required. The treatments should be spaced by appropriate intervals, for example, 2-3 weeks. Alternatively, fewer treatments could be administered at or close to the maximum non-toxic dosage. Again, commencement of gamma-interferon therapy prior to parasite invasion is preferred. No ill effects were observed in any of the animals treated in the experiments described here.

A preliminary recommended per-treatment dosage for humans is $5 \times 10^6$ units of interferon daily for 5 days preferably beginning on the day prior to exposure to the disease, or, alternatively, beginning on the day of exposure. This corresponds to 0.25 mg of gamma-IFN, assuming a specific activity of $2 \times 10^7$ units/mg. Higher doses are permissible provided that they are not toxic. Lower doses may also be effective. It is thus contemplated that the amount of gamma-interferon to be administered will vary and may vary from patient to patient and according to the severity of the infection or the magnitude of the risk of infection. Establishment of the particular dosage forms, however, is a matter of routine experimentation and well within the skill of the art.

A related application of the present invention is in combatting "dormant" forms of malarial infection, such as that due to P. vivax or P. ovale. Some exoerythrocytic forms of these species remain viable in the human liver for long periods after the elmination of the blood stages. Primaquine (an 8-amino quinoline) is the only available therapeutic agent that attacks these liver stages. Thus, gamma-interferon will be effective in destroying remaining dormant forms of the parasite and preventing clinical relapses. The method of treatment will be the same as in first infection cases, and should be commenced and completed during the dormant stage. This would not be difficult to accomplish given that the dormant stage usually lasts for months or even years.

It is clear from this discussion that gamma-interferon will also be effective as an adjunct to immunization and/or drug therapy.

For example, gamma-interferon can be used prophylactically in humans either alone or in conjunction with human monoclonal antibodies against blood-stages or sporozoite (passive immunization). Currently available monoclonal antibodies against sporozoites are successful in achieving a 95% inhibition of parasitemia in experimental animals. This figure could be made 100% if the monoclonal antibodies are used together with gamma-interferon.

The preferred regimen will be administration of anti-sporozoite antibodies prior to exposure to the parasite together with and/or followed by administration of gamma-interfer feron before and/or after exposure to sporozoites. Gamma-interferon may be administered prophylactically in conjunction with a drug. The interferon regimen will be as outlined above and the drug regimen will be as normally prescribed according to well-known dosages.

Another way that gamma-interferon can be used is in conjunction with a vaccine. Immunization can take place initially with or without interferon. Then interferon can be administered when the mammal is in an endemic area and exposed to sporozoite infection. Interferon therapy can be continued after the mammal leaves the endemic area for a period of time sufficient to avoid patency (assuming of course no re-infection). Finally, interferon can be used in conjunction with drug therapy (or with both immunization and drug therapy). In that case, interferon will be administered initially (before and/or after infection). If, despite interferon therapy, the mammal becomes patent, drugs will be used to combat the blood stage of the disease. (An anti-merozoite vaccine, if one is developed, might also be used in conjunction with gamma-interferon).

EXAMPLE 4

DNA Extraction, Purification and Assay as a Measure of Sporozoite Infectivity

In order to obtain sporozoites for use in the experiments described in this application, P. berghei sporozoites (Nk 65 strain), maintained by cyclic passage of the parasite through Anopheles stephensi mosquitoes were collected 14 to 18 days after an infective blood meal by dissecting the salivary glands into Medium 199 (GIBCO, Grand Island, NY) containing 10% heat-inactivated normal rat serum and injected into the dorsal tail vein or the portal vein of the mammals.

Forty- to fifty-day old female Norway Brown rats (Harlan Sprague Dawley, Indianapolis, IN) were bled from the axillary vein and artery. Livers were perfused with cold PBS, removed and frozen in liquid $N_2$. To purify the DNA, livers were homogenized in the presence of 150 mM NaCl, 10 mM EDTA, 1% w/v SDS, followed by the addition of sodium perchlorate to 0.5M. Two organic solvent extractions were performed, the first with 1 volume of a chloroform-isoamyl alcohol mixture, and the second with 1 volume of a chloroform-isoamyl alcohol-phenol mixture. The DNA in the aqueous phase was ethanol-precipitated, spooled onto a glass rod, dissolved in water, treated with RNAase (Boehringer Mannheim, Indianapolis, IN), alpha-amylase (type II-A, Sigma Chemical Company, St. Louis, MO) and proteinase K (BRL, Gaithersberg, MD), reprecipitated with ethanol, redissolved in water, and the concentration was measured at 260 mM. In order to obtain blood stages of Plasmodium berghei DNA, female A/J mice (Jackson Laboratories, Bar Harbor, ME) were injected with 5,000 P. Berghei sporozoites. Ten days after injection the animals were bled in the presence of heparin. The blood was spun down and the buffy coat removed. The pellet was washed, resuspended and passed through a glass wool column. The purified red cells were treated with 0.015% (w/b) Saponin (Sigma, St. Louis, MO) and incubated at 37° C. for 15 minutes. The released parasites were washed with PBS, homogenized in the presence of 10 mM Tris-HCl, pH 8.0, 10 mM NaCl, 10 mM EDTA and 0.5% SDS. After treatment with proteinase K, this material was extracted twice with a chloroform-isoamyl alcohol-phenol mixture as above and precipitated with ethanol. This was followed with a second cycle of proteinase K-RNAase treatment, organic solvent extraction and ethanol precipitation. The pellet was dissolved in the water and the DNA concentration measured. Serial dilutions of DNA were immobilized onto nitrocellulose filters and hybridized with a probe. Preparation of the probe is described below.

DNA samples were denatured at room temperature in the presence of 100 mM NaOH. After neutralization with 80 mM $NaH_2PO_4$ and adjusting the concentration to 6× sodium chloride, sodium citrate solution (SSC) (1×SSC: 150 mM NaCl, 15 mM sodium citrate), 200 micrograms total DNA were immobilized per each 2.5 cm diameter, 0.45 millimicron pore-size nitrocellulose filter (Millipore Corp., Bedford, MA). The filters were dried under an infrared lamp, baked under vacuum at 80° C. for two hours, presoaked for four hours at 42° C. in a mixture containing 5× SSC, 1× Denhardt's solution (1× Denhardt's solution (1× Denhardt's: 100 mg Ficoll, 100 mg polyvinylpyrrolidone, 100 mg bovine serum albumin,, $H_2O$ to 10 ml), 0.1 mg per ml denatured salmon testes DNA (Sigma, St. Louis, MO) 0.2 mg per ml RNA (from Torula yeast, type VI, Sigma) 20 mM HEPES (Sigma) and 50% formamide.

Hybridization with $^{32}P$-labeled DNA probe ($3 \times 10^6$ cpm per filter) was carried out at 42° C. for 15 hours. The filters were washed for five minutes at room temperature with 2× SSC, 0.5% SDS; 15 minutes with 2× SSC, 0.1% SDS; followed by four washes at 54° C., 30 minutes each, with 0.4× SSC, 0.5% SDS. After drying, the bound radioactivity was determined by scintillation counting.

Figure 4:
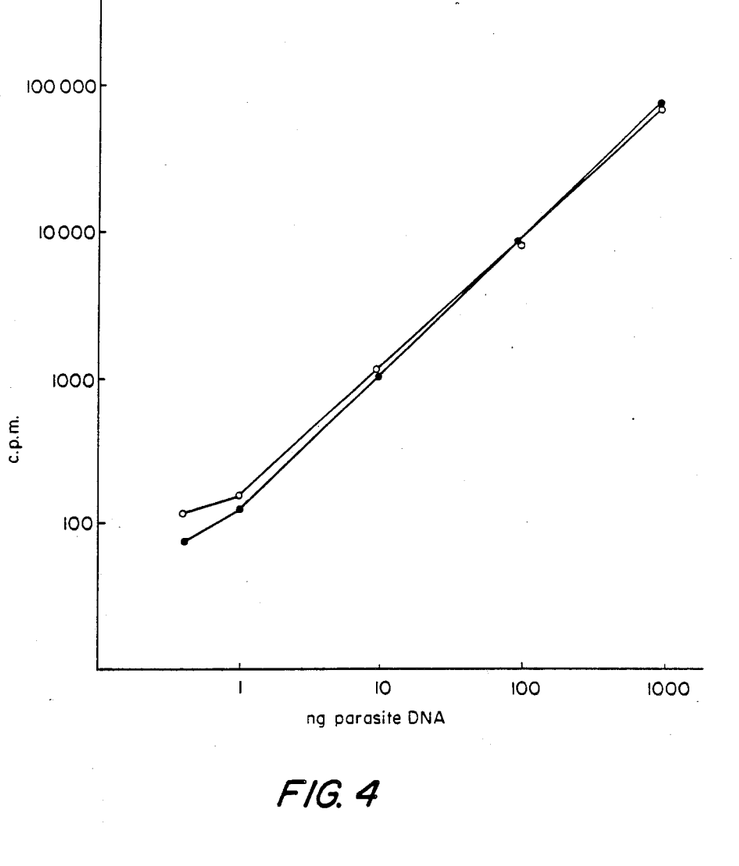
FIG. 4 is a graph showing the relationship between DNA concentration and the amount of radioactivity retained by filters after hybridization using the assay for EEF development of the present invention.

As can be seen in FIG. 4, a linear relationship existed between the amount of DNA bound to the filter and the amount of radioactivity retained after hybridization. This linear relationship existed between 100 pg to one microgram of P. berghei DNA immobilized on nitrocellulose filters. The open circles and the closed circles in FIG. 4 represent the results of two different experiments. Each value represents the mean of three filters. Standard deviations were negligible.

The above data demonstrate the utility of this assay for the detection of sporozoite DNA. This method permits detection of 100 pg of parasite DNA, or 1,000 haploid nuclei, assuming that each nucleus contains 0.1 pg of DNA. Therefore, the minimum number of parasites detectable per liver is about 62,500. This represents the progeny of only 6-7 sporozoites at their peak of proliferation, since each sporozoite can generate close to $10^4$ haploid nuclei after 13 nuclear divisions. Therefore, this assay is very sensitive and ideally suited to measure the effect of antisporozoite agents and vaccines.

EXAMPLE 5

Preparation and Labeling of DNA Probe

In the discussions below, all enzymes used in the practice of the present invention are commercially available from New England Nuclear (Boston, MA), New England Biolabs (Beverly, MA) or Boehringer Mannheim (Indianapolis, IN).

The DNA probe (p-263-1) used to assay sporozoite infectivity was prepared as follows: A 2.2 Kb sequence of P. berghei origin was obtained from a pBR322/BamH1 library containing Sau3A fragments of P. berghei total DNA. This element is present in at least 100 copies in the genoma of P. berghei as determined by standard dot blot hybridization. Total P. berghei sporozoite DNA was digested with Sau3A and fractionated on a 1% low melting point agarose (IBI, New Haven, CT) gel. The 2.2 kb region of the gel was excised and the DNA recovered by melting the agarose and extracting the DNA according to the manufacturers instructions.

An aliquot of the sample was cloned into pBR322 which had been digested with BamH1, using techniques well known in the art (BamH1 digestion leaves cohesive ends which can be ligated with Sau3A-digested samples. See Maniatis et al., Molecular Cloning, A Laboratory Manual, p. 101, Cold Spring Harbor Laboratory, Cold Spring Harbor, New York, 1982). Another aliquot obtained as above, was radiolabeled with $^{32}P$ by nick translation as described (Ferreira et al, Mol. Biochem. Parasitol, 19: 103–109, 1986, incorporated by reference).

The resulting pBR322/BamH1 library was screened with the radiolabeled probe ($4 \times 10^5$ cpm/ml; specific activity $5 \times 10^7$ cpm/ug). One of the several positive clones was picked and amplified. Plasmid DNA (p-263-1) was prepared from this clone by alkaline lysis and $C_sCl$ gradient centrifugation as described (Maniatis, et al., supra, pp. 90–91, incorporated by reference). This plasmid was radiolabelled by nick translation as above, and used for standard dot blue hybridizations.

The present invention has been described above by reference to preferred embodiments. It is understood that many additions, deletions and modifications will be apparent to one of ordinary skill in the art in light of the present description without departing from the scope of the invention, as claimed below.

What is claimed is:

1. A method for inhibiting the development or limiting the extent of malarial parasitemia in mammals comprising administering to a mammal in need of such treatment before the onset of parasitemia in said mammal an amount of gamma-interferon sufficient to inhibit parasitemia, said parasitemia being incident to invasion of said mammal by sporozoites of a member of the genus Plasmodium, said administration taking place no later than the end of the prepatency period of said mammal.

2. The method of claim 1 comprising parenterally administering said interferon.

3. The method of claim 1 comprising administering said interferon before said mammal becomes invaded by said sporozoites.

4. The method of claim 1 comprising administering said interferon after said mammal becomes thus invaded.

5. The method of claim 1 comprising administering to said mammal interferon at least once before said mammal becomes thus invaded and repeating said interferon administration at least once after said mammal becomes thus invaded.

6. The method of claim 1 comprising administering to said mammal an amount of gamma-interferon within the range between about 10 and about 15 million units per 5-day treatment.

7. The method of claim 6 wherein said mammal is a primate.

8. A method of inhibiting development of exoerythrocytic forms of malarial sporozoites, in a mammal, wherein development of said forms is incident to invasion of said mammal by said sporozoites, comprising administering to said mammal an amount of gamma-interferon effective to inhibit development of said exoerythrocytic forms.

9. The method of claim 8 comprising administering said interferon prior to invasion of said mammal by said sporozoites.

10. The method of claim 8 comprising administering said interferon after invasion of said mmmal by said sporozoites.

11. The method of claim 8 comprising administering said interferon at least once before and at least once after said invasion.

12. The method of claim 8 comprising administering to said mammal an amount of gamma-interferon within the range between about $2 \times 10^6$ and about $5 \times 10^6$ units per day.

13. The method of claim 12 wherein said mammal is a primate.

14. A method for preventing malaria infection in a mammal in need of such treatment comprising administering to said mammal an amount of gamma-interferon effective for preventing malaria infection to said mammal, said infection being incident to invasion of said mammal by sporozoites of a member of the genus Plasmodium.

15. The method of claim 14 comprising administering said interferon prior to invasion of said mammal by said sporozoites.

16. The method of claim 14 comprising administering said interferon after invasion of said mammal by said sporozoites.

17. The method of claim 14 comprising administering said interferon at least once before and at least once after said invasion.

18. The method of claim 14 wherein said mammal is a primate, said method comprising administering to said mammal an amount of interferon within the range between about 50 and about 10 million units per treatment.

19. A method for preventing malaria infection in a mammal comprising administering an amount of gamma-interferon effective for preventing malaria infection in said mammal in conjunction and substantially contemporaneously with at least one anti-malarial drug selected from the group consisting of chloroquine, pyrimethanine and combinations thereof.

* * * * *